United States Patent [19]
Matson

[11] Patent Number: 6,011,156
[45] Date of Patent: Jan. 4, 2000

[54] PROCESS FOR REMOVING PRIMARY AMINES FROM AN AMINE-CONTAINING STREAM

[75] Inventor: Michael S. Matson, Bartlesville, Okla.

[73] Assignee: Phillips Petroleum Company, Bartesville, Okla.

[21] Appl. No.: 09/329,987

[22] Filed: Jun. 8, 1999

[51] Int. Cl.[7] .................... C07D 295/023; C07C 209/84; C07C 209/86
[52] U.S. Cl. ........................... 546/184; 564/437; 564/499
[58] Field of Search ............................ 546/184; 564/499, 564/437

[56] References Cited

U.S. PATENT DOCUMENTS

| | | |
|---|---|---|
| 4,306,068 | 12/1981 | Smith, Jr. ................................. 546/184 |
| 4,544,749 | 10/1985 | Ayusawa et al. ....................... 546/184 |
| 4,605,742 | 8/1986 | Mori et al. .............................. 546/184 |

*Primary Examiner*—Bernard Dentz
*Attorney, Agent, or Firm*—Polly C. Owen

[57] ABSTRACT

A process is provided for removing primary amines from an amine-containing stream. Particularly, a process is provided for removing primary amines from said amine-containing stream by reacting said primary amine with a dione. More particularly, a process is provided for removing n-amylamine from an amine-containing stream comprising piperidine by reacting n-amylamine with 2,5-hexanedione.

7 Claims, No Drawings

PROCESS FOR REMOVING PRIMARY AMINES FROM AN AMINE-CONTAINING STREAM

FIELD OF INVENTION

This invention relates to the field of processes for removing primary amines from an amine-containing stream. Particularly, this invention relates to a process for removing primary amines from said amine-containing stream by reacting said primary amine with a dione. More particularly, this invention relates to a process for removing n-amylamine from an amine-containing stream comprising piperidine by reacting n-amylamine with 2,5-hexanedione.

BACKGROUND OF THE INVENTION

During the production of secondary amines, primary amines can also be produced. For example, in the production of piperidine, n-amylamine is also produced. Often times, customers demand that secondary amine products contain very small quantities of primary amine. For example, product specifications for the amount of n-amylamine in piperidine can be as low as 0.1% by weight. Removing primary amines from secondary amines is not a simple process since the boiling points of primary amines and secondary amines of similar molecular weight can vary by only a few degrees Celsius. For example, the boiling point of n-amylamine is 104° C. while the boiling point of piperidine is 106° C.

Several chemical reaction schemes have been proposed to remove primary amines from secondary amines. One such reaction scheme involves a reaction of an aldehyde or ketone with a primary amine to form an "imine". This reaction scheme may be represented by:

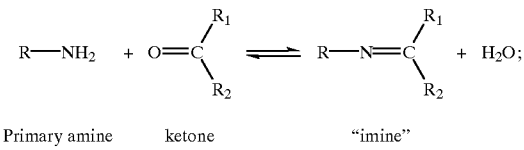

Primary amine    ketone    "imine"

where $R_1$ and $R_2$ can be the same or different and are selected from the group consisting of hydrocarbyl radicals having from 1 to about 10 carbon atoms per radical. This reaction is reversible, and the water must be removed to drive the reaction to completion. One method of removing the water is to add benzene or cyclohexane to high boiling ketones to azeotrope with water. Then, the secondary amine can be removed by distillation. This reaction scheme is cumbersome due to the requirement of removing water and the difficulty in separating the imine and aldehyde or ketone from the secondary amine. Furthermore, secondary amines can react with the aldehyde or ketone in an equilibrium reaction lowering the amount of secondary amine produced.

A process is needed to efficiently separate primary amines from secondary amines. This invention provides such a process.

SUMMARY OF INVENTION

It is an object of this invention to provide a process for removing primary amines from an amine-containing stream.

It is also an object of this invention to provide a process for removing primary amines from an amine-containing stream by reacting said primary amine in said amine-containing stream with a dione.

It is another object of this invention to provide a process for removing n-amylamine from an amine-containing stream comprising piperidine by reacting n-amylamine with 2,5-hexanedione.

It is yet another object of this invention to provide a process for removing n-amylamine to levels below 0.1% by weight from an amine-containing stream comprising piperidine.

In accordance with this invention, a process for removing primary amines from an amine-containing stream is provided, said process comprising (or optionally, "consisting essentially of", or "consisting of"):
1) reacting said primary amines in said amine-containing stream with a dione to produce a first mixture;
    wherein said amine-containing stream comprises primary amines and secondary amines;
    wherein said dione has the formula:

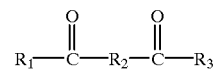

wherein $R_1$ and $R_3$ are the same or different and are selected from the group consisting of hydrocarbyl radicals having from 1 to 10 carbon atoms per radical;
   wherein $R_2$ is selected from the group consisting of hydrocarbyl radicals having from 2 to 6 carbon atoms per radical;
   wherein said first mixture comprises said secondary amine and a reaction product of said dione and said primary amine.
2) separating said first mixture to produce at least one amine-rich stream and at least one amine-lean stream;
    wherein said amine-rich stream comprises said secondary amines; wherein said amine-lean stream comprises said reaction product of said dione and said primary amine.

These objects and other objects of this invention will become more apparent with reference to the following.

DETAILED DESCRIPTION OF INVENTION

In this invention, a process is provided for removing primary amines from an amine-containing stream, said process comprising:
1) reacting said primary amines in said amine-containing stream with a dione to produce a first mixture; and
2) separating said first mixture to produce at least one amme-rich stream and at least one amine-lean stream.

Said amine-containing stream comprises primary amines and secondary amines. Amines are a class of organic compounds of nitrogen that may be considered as derived from ammonia ($NH_3$) by replacing one or more of the hydrogen atoms with alkyl groups. The amine is primary if one of the hydrogen atoms is replaced, secondary if two hydrogen atoms are replaced, and tertiary if three hydrogen atoms are replaced. Said amine-containing stream can further comprise tertiary amines. Preferably, said secondary amine is piperidine. Most preferably, said secondary amine is piperidine, and said primary amine is n-amylamine.

Said dione is represented by the formula:

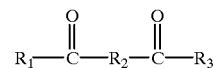

where $R_1$ and $R_3$ can be the same or different and are selected from the group consisting of hydrocarbyl radicals having from 1 to 10 carbon atoms per radical. $R_2$ is selected from the group consisting of hydrocarbyl radicals having from 2 to 6 carbon atoms per radical. Preferred diones are selected from the group consisting of 2,5-hexanedione; 2,6-heptanedione, and 2,7-octanedione. The most preferred dione is 2,5-hexanedione since it reacts with n-amylamine to produce an intermediate imine, and the intermediate imine then reacts to produce N-amyl-2,5-dimethylpyrrole. N-amyl-2,5-dimethylpyrrole is a stable compound and can be easily removed from said secondary amine. Unlike other reactions of aldehydes and ketones with primary amines, the production of the pyrrole drives the intermediate equilibrium reaction to completion. This is a great advantage since water does not have to be removed to drive the reaction to completion.

Said amine-containing stream and said dione are reacted by any means known in the art to produce said first mixture. For example, said amine-containing stream and said dione can be mixed in a vessel or tank. Said amine-containing stream and said dione are contacted for a sufficient time to cause said primary amines and said dione to react to produce a reaction product. Said first mixture comprises said secondary amine and said reaction product of said primary amine and said dione. Depending on the concentrations of the primary amines and dione, contact times can vary from 1 minute to hours.

Step 2 is separating said first mixture to produce at least one amine-rich stream and at least one amine-lean stream. Said amine-rich stream comprises said secondary amines. Said amine-lean stream comprises said reaction product of said dione and said primary amine. Said amine-lean stream can further comprise at least one compound selected from the group consisting of water and hydrocarbons having from 1 to about 5 carbon atoms.

The separating can be accomplished by any means in the art. Particularly, in the removal of n-amylamine from an amine-containing stream comprising piperidine, the separating can be accomplished by distillation producing a first amine-lean stream comprising a small portion of the piperidine, water, and hydrocarbons having from 1 to about 5 carbon atoms, an amine-rich stream comprising substantially all of the piperidine, and a second amine-lean stream comprising N-amyl-2,5-dimethylpyrrole.

EXAMPLES

Example 1

100 grams of an amine-containing stream containing 98.93 grams of piperidine and 1.097 grams of n-amylamine were placed in a 200 cc flask with stirring bar. 3.5 grams of 2,5-hexanedione were added to said amine-containing stream to produce a first mixture. The first mixture was immediately sampled. The first mixture was then stirred at ambient temperature and sampled periodically. The course of the reaction was monitored by gas chromatography, and the results of the various samples are shown in Table 1.

The data demonstrate that the 2,5-hexanedione reacts to form an intermediate imine which then reacts with loss of additional water to form N-amyl-2,5-dimethylpyrrole. There was no detected reaction product for piperidine and 2,5-hexanedione, therefore the piperidine yield was not lowered by the removal of n-amylamine using 2,5-hexanedione.

Example 2

1306.2 grams of an amine-containing stream containing 1295.7 grams of piperidine and 0.184 weight % n-amylamine were charged to a distillation kettle. 7.88 grams of 2,5-hexanedione were also added to the distillation kettle to produce a first mixture. The kettle was heated until the first mixture reached reflux at which point the kettle temperature was 106° C., and the reflux temperature was 89° C. The reaction mixture was allowed to reflux for about 4 hours before a first amine-lean stream comprising a small portion of the piperidine, water, and hydrocarbon having from 1 to about 5 carbon atoms was removed overhead at a reflux ratio of 10:2. 31.4 grams of said first amine-lean stream were taken overhead at the 10:2 ratio. At this point, the head temperature of the distillation column was 105° C. Then, 1210.5 grams of a second amine-rich stream comprising substantially all of the piperidine were taken overhead at a reflux ratio of 3:2 in the temperature range of 105–106° C. The second amine-rich stream contained 99.90 % by weight piperidine and 0.027 % by weight n-amylamine. The kettle still contained 69.2 grams of said amine-containing stream which was 73.79 % by weight piperidine, 3.46 % by weight 2,5-hexanedione, and 7.328% by weight N-arnyl-2,5-dimethyl pyrrole. 93.4% by weight of the piperidine in the amine-containing stream was recovered. There was no detected n-amylamine in the kettle. Also, there were no other species present that was the reaction product of piperidine with 2,5-hexanedione.

This example demonstrates that an amine-containing stream that contains n-amylamine can be reacted with 2,5-hexanedione and distilled to produce said second amine-rich stream containing >99.5 % by weight piperidine and <0.1% n-amylamine. In addition, 93.4 % by weight of the piperidine in the amine-containing stream was recovered in the second amine-rich stream.

TABLE 1

| Time (hours) | n-amylamine (wt. %) | Piperidine (wt. %) | 2,5-Hexane-dione (wt. %) | Imine Intermediate (wt. %) | N-amyl-2,5-dimethyl-pyrrole (wt. %) |
| --- | --- | --- | --- | --- | --- |
| 0.05 | 1.1359 | 95.5917 | 2.6497 | 0.0344 | 0.0068 |
| 1.00 | 0.6825 | 95.4329 | 2.2360 | 0.6936 | 0.3160 |
| 2.10 | 0.4402 | 95.4204 | 1.9604 | 0.8775 | 0.5650 |
| 3.50 | 0.2679 | 95.4295 | 1.7882 | 0.8097 | 0.9364 |
| 5.75 | 0.1652 | 95.3153 | 1.6571 | 0.5875 | 1.3923 |
| 7.50 | 0.1071 | 95.3654 | 1.6077 | 0.4475 | 1.6577 |
| 11.60 | 0.0468 | 95.4379 | 1.5291 | 0.2496 | 1.9712 |
| 23.50 | 0.0086 | 95.3375 | 1.5206 | 0.0528 | 2.3565 |
| 26.50 | 0.0051 | 95.2739 | 1.5200 | 0.0350 | 2.4042 |

That which is claimed is:

1. A process for removing primary amines from an amine-containing stream, said process comprising:

1) reacting said primary amines in said amine-containing stream with a dione to produce a first mixture;

wherein said amine-containing stream comprises primary amines and secondary amines;

wherein said dione has the formula:

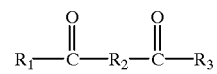

wherein $R_1$ and $R_3$ are the same or different and are selected from the group consisting of hydrocarbyl radicals having from 1 to 10 carbon atoms per radical;

wherein $R_2$ is selected from the group consisting of hydrocarbyl radicals having from 2 to 6 carbon atoms per radical;

wherein said first mixture comprises said secondary amine and a reaction product of said dione and said primary amine.

2) separating said first mixture to produce at least one amine-rich stream and at least one amine-lean stream;

wherein said amine-rich stream comprises said secondary amines;

wherein said amine-lean stream comprises said reaction product of said dione and said primary amine.

2. A process according to claim 1 wherein said diones are selected from the group consisting of 2,5-hexanedione; 2,6-heptanedione, and 2,7-octanedione.

3. A process according to claim 2 wherein said secondary amine is piperidine.

4. A process according to claim 3 wherein said dione is 2,5-hexanedione.

5. A process according to claim 4 wherein said primary amine is n-amylamine.

6. A process according to claim 5 wherein said amine-lean stream can further comprise at least one compound selected from the group consisting of water and hydrocarbons having from 1 to about 5 carbon atoms.

7. A process according to claim 6 wherein said separating is accomplished by distillation.

* * * * *